(12) United States Patent
Belt

(10) Patent No.: US 11,536,397 B2
(45) Date of Patent: Dec. 27, 2022

(54) ANTI-KINKING DEVICE

(71) Applicant: Payten Belt, Beach City, TX (US)

(72) Inventor: Payten Belt, Beach City, TX (US)

( * ) Notice: Subject to any disclaimer, the term of this patent is extended or adjusted under 35 U.S.C. 154(b) by 163 days.

(21) Appl. No.: 16/798,806

(22) Filed: Feb. 24, 2020

(65) Prior Publication Data
US 2021/0262590 A1   Aug. 26, 2021

(51) Int. Cl.
*F16L 3/12* (2006.01)
*F16L 3/10* (2006.01)

(52) U.S. Cl.
CPC .......... *F16L 3/1226* (2013.01); *F16L 3/1075* (2013.01)

(58) Field of Classification Search
CPC ......... F16L 3/1226; F16L 3/1075; F16L 3/01; F16L 3/237; F16L 3/22
USPC .......... 138/106, 110, DIG. 8; 248/68.1, 67.7, 248/74.1, 74.4, 65, 49, 302, 75, 80, 84, 248/86, 88; 403/391, 396; 174/43; 285/419, 114–116, 415, 412, 373, 368
See application file for complete search history.

(56) References Cited

U.S. PATENT DOCUMENTS

| | | | | |
|---|---|---|---|---|
| 1,539,001 A * | 5/1925 | Steeple | ................... | F16L 33/04 285/259 |
| 2,172,130 A * | 9/1939 | Powell | ................... | A01G 25/00 138/110 |
| 2,963,305 A * | 12/1960 | Miller | ................... | F16L 33/04 24/339 |
| 3,252,192 A * | 5/1966 | Smith | ................... | F16L 1/10 138/99 |
| 3,295,548 A * | 1/1967 | Woods | ................... | A01G 25/00 D15/27 |
| 3,982,779 A * | 9/1976 | Hickey | ................... | F16L 21/06 403/311 |
| 4,093,282 A * | 6/1978 | Kyriakodis | ............. | F16L 33/08 285/259 |
| 4,492,391 A * | 1/1985 | Haines | ................... | F16L 21/08 285/368 |
| 5,090,742 A * | 2/1992 | Cohen | ................... | F16L 21/08 285/373 |
| 5,580,102 A * | 12/1996 | Stultz | ................... | F16L 3/18 248/901 |
| 6,139,068 A * | 10/2000 | Burress | ................. | F16L 19/005 285/92 |
| 8,061,390 B2 * | 11/2011 | Condon | ................... | E03C 1/021 248/214 |

(Continued)

FOREIGN PATENT DOCUMENTS

| | | |
|---|---|---|
| JP | 2015-139560 | 8/2015 |
| WO | 2018/135686 | 7/2018 |

OTHER PUBLICATIONS

International Search Report and Written Opinion dated Jun. 15, 2021 in corresponding PCT Application No. PCT/US2021/070180.

*Primary Examiner* — Ingrid M Weinhold
(74) *Attorney, Agent, or Firm* — Hogan Lovells US LLP

(57) ABSTRACT

Kinking of tubing can be prevented by use of a device comprising a first clamp, a second clamp, a first rod and a second rod. The first clamp and the second clamp carry the first rod and the second rod to form a frame, and the flexible tubing is secured to the first clamp and the second clamp. The device can be easily moved and adjusted by a user. The device can be attached to any location along the tubing and allow the tubing to bend past 90 degrees without kinking. Multiple devices can be used in series to route tubing in desired route without it kinking.

13 Claims, 13 Drawing Sheets

(56) References Cited

U.S. PATENT DOCUMENTS

| | | | |
|---|---|---|---|
| 8,181,999 B2* | 5/2012 | Cromarty | F16L 25/0018 |
| | | | 285/419 |
| 8,205,804 B2* | 6/2012 | Parker | F16L 55/005 |
| | | | 248/65 |
| 9,182,001 B2* | 11/2015 | Pesek | F04D 29/669 |
| 9,383,039 B2* | 7/2016 | Hirst | F16L 3/1207 |
| 9,534,708 B2* | 1/2017 | Cripps, II | F16L 3/221 |
| 9,534,718 B2* | 1/2017 | O'Neil | F16L 21/065 |
| 10,830,263 B2* | 11/2020 | Logan | F16B 2/06 |
| 2010/0213326 A1* | 8/2010 | Julian | E03C 1/021 |
| | | | 248/72 |
| 2010/0314870 A1* | 12/2010 | Cromarty | F16L 25/0018 |
| | | | 285/420 |
| 2012/0321408 A1 | 12/2012 | Ewles | |
| 2014/0061393 A1* | 3/2014 | Cripps, II | F16L 3/221 |
| | | | 248/62 |
| 2017/0059069 A1 | 3/2017 | Rempert | |
| 2019/0376623 A1 | 12/2019 | Loewe | |

* cited by examiner

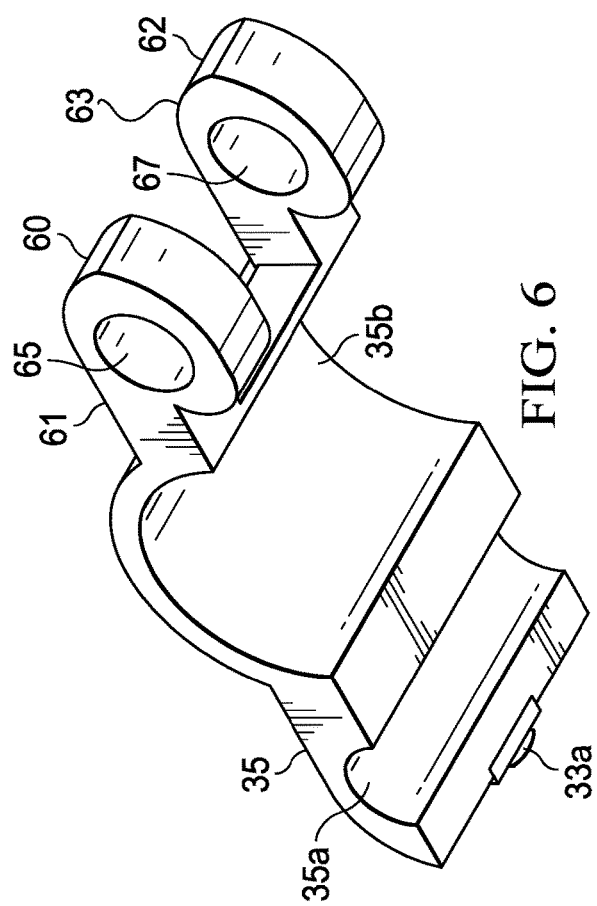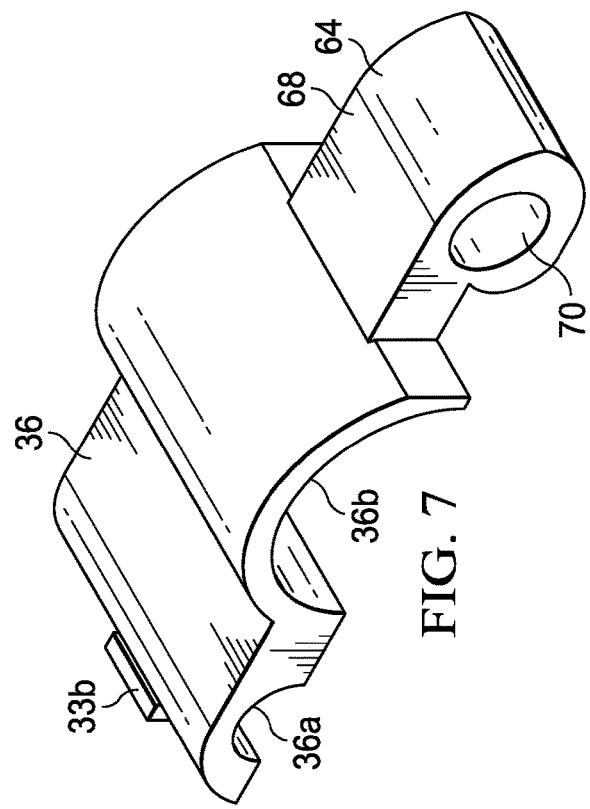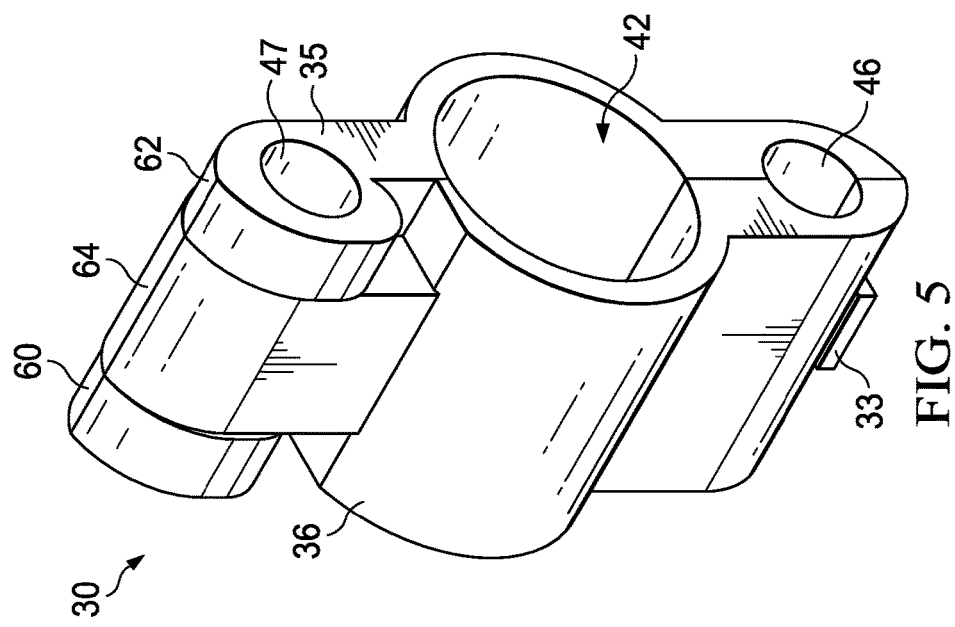

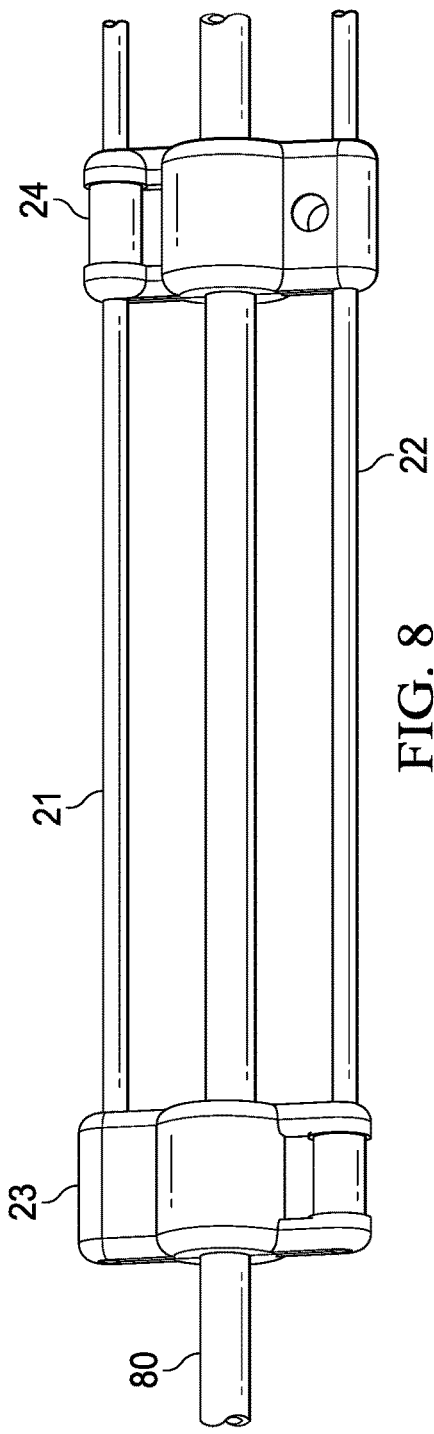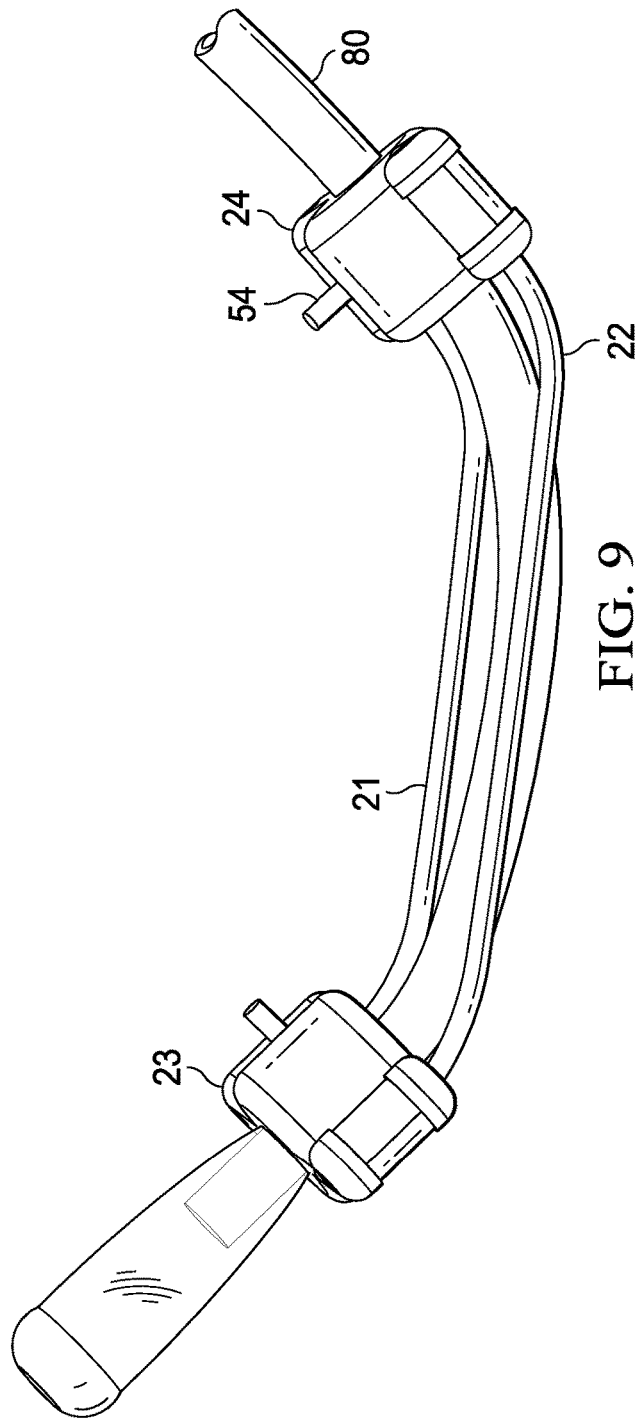

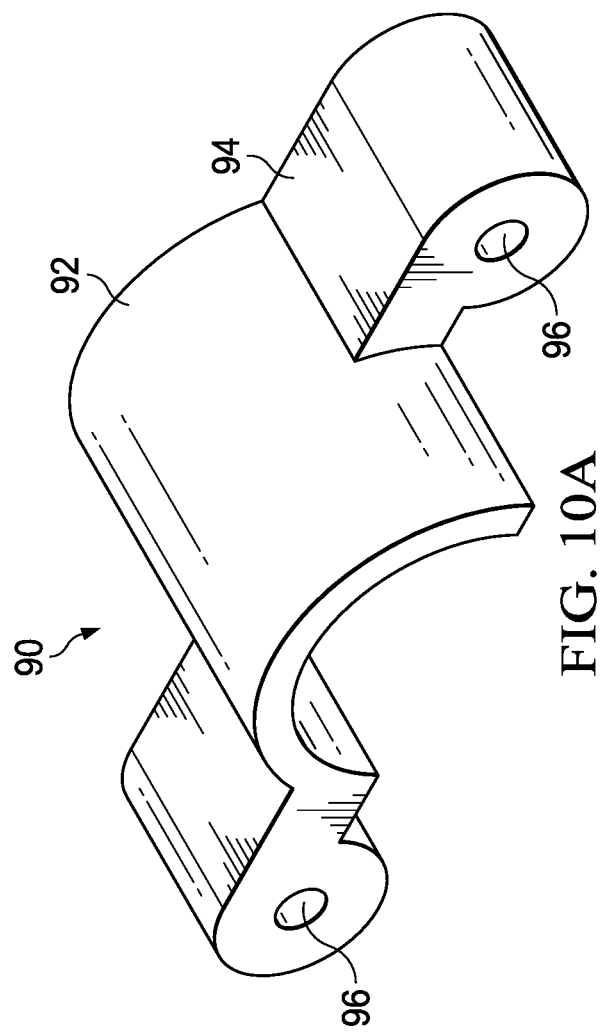
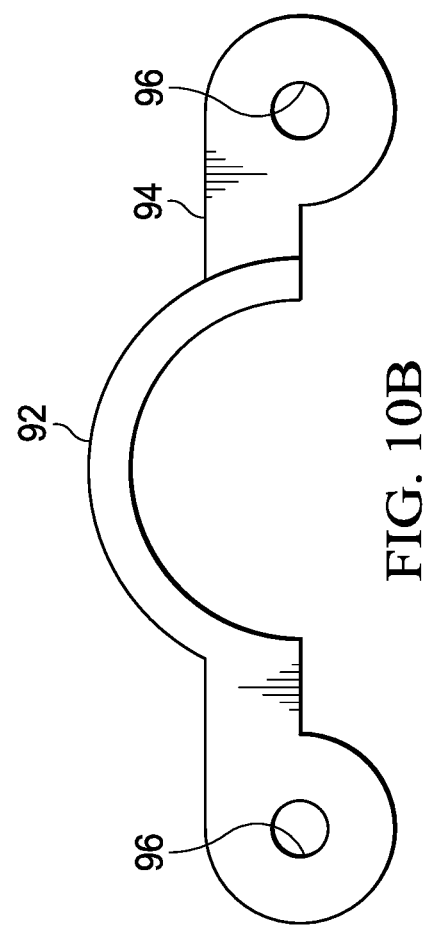
FIG. 10A
FIG. 10B

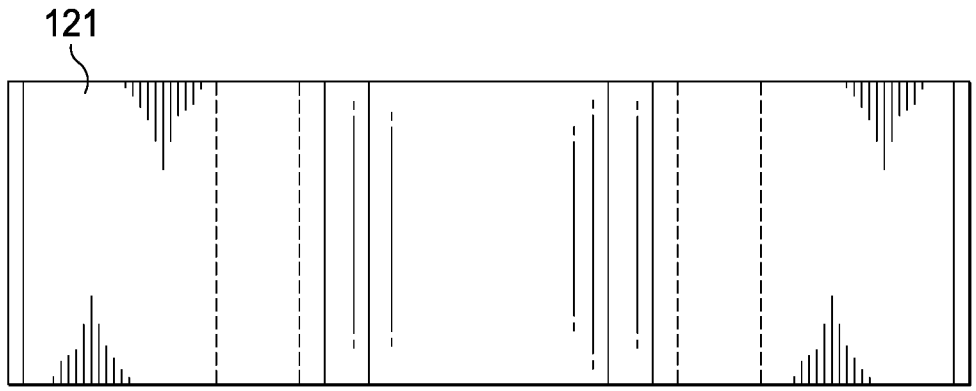
FIG. 12A
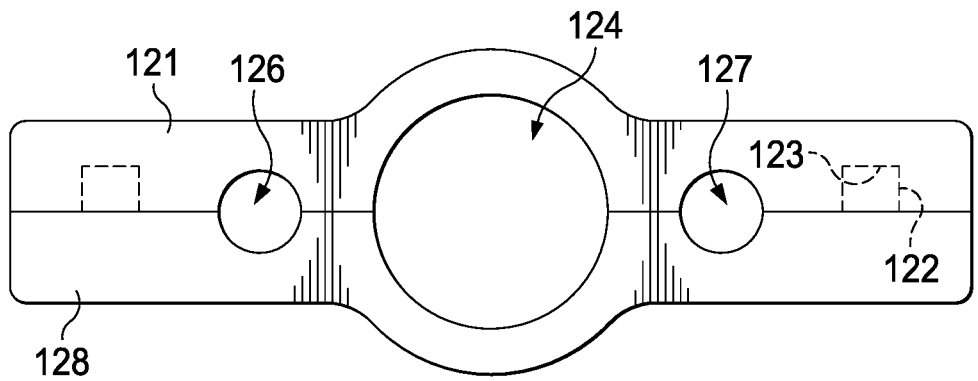
FIG. 12B
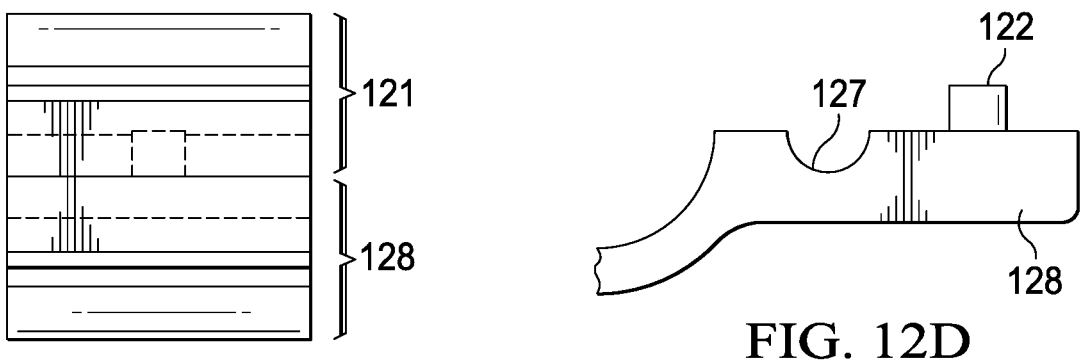
FIG. 12C
FIG. 12D

ANTI-KINKING DEVICE

FIELD

The disclosure relates generally to kink-resistant devices. The disclosure relates specifically to an anti-kinking device that reduces kinking of tubing or hoses.

BACKGROUND

Flexible tubing or hoses are widely utilized in countless applications. For instance, garden hoses are used for watering grass, trees, shrubs, flowers, vegetable plants, vines, and other types of vegetation. Many medical devices use some sort of tubing. Oxygen delivery, intravenous (IV) catheters, hemodialysis equipment, and feeding pumps rely on a wide variety of tubing to carry oxygen, blood, medicine, and other liquids or gases.

Kinking is a phenomenon that may occur when the tubing is doubled over or twisted. A consequence of kinking is that the flow of fluid or gas through the hose can be either severely restricted or blocked. Kinking is a nuisance that causes the user to waste time unkinking the hose and can be deadly. The user or caregiver must then attempt to remove the blockage by manual manipulation, such as by swinging the tubing to relax the kink or approaching the kinked location and manually straightening the kink.

Kinking is especially problematic in medical tubing where interrupted or substantially constrained flows can mean that important gases or fluids are not delivered as expected. For example, it has been estimated that about 800,000 patients are receiving HOT (home oxygen therapy) according to Kira, S and Petty, T L. Progress in domiciliary respiratory care: Current Status and Perspective (1994). When traveling with portable units, the tubing to supply oxygen is often damaged by the backpacks and sacks used to support the device. Oxygen tubing kinks in many places along the tubing and near the connecting ports, this kinking restricts airflow and can be a critical problem. Portable oxygen therapy patients tend to have trouble with the damage of the tubing when it comes in contact with the backpack that houses the oxygen device. Oxygen tubing are especially prone to kinking as the tubing may get twisted and otherwise kinked as the patient moves around or rolls over in a bed.

Noncontact oxygen delivery method such as "wafting" oxygen has been developed to overcome kinking during the period of delivering oxygen to a patient. By wafting the oxygen, the patient does not need to be in contact with the machine or a mask to inhale the oxygen.

Although this method works well for most, there is an issue with the air flow becoming compromised, it can never replace properly administered oxygen (Davies, P. "The Efficacy of Noncontact Oxygen Delivery Methods" Pediatrics (November 2002)).

One proposed solution for kinking is disclosed in U.S. Pat. No. 8,752,591 to Anthony. Referring to FIG. 1, Anthony provides a spiral metal wire 14 to wrap around the hose 40 such that the metal wire 14 is sufficiently thick and ridged to prevent kinking of the hose 40. While this proposed solution does reduce the likelihood of a kink, it suffers from numerous drawbacks. One such drawback is that the wire adds significant weight to the tubing, thereby making the tubing difficult to carry. Another disadvantage is that the ridged wire reduces flexibility of the hose thereby reducing its ability to bend and move around a corner or obstacle. A further drawback is that if the hose does kink, it is likely to permanently bend the wire, which in turn permanently established the kink at that location.

Wire braiding can also be used to make medical tubing with more kink-resistant and improve burst strength. Small tubing is often required in the medical field, but the smaller the tubing the less reliable it is and the more prone to kink (Weber, A., "Tackling tubing: tiny tubing presents big challenges", Medical Device Assembly, January 2010). Therefore, although wire braiding works well for some medical tubing, there is an issue with a small tubing having a very thin wall thickness.

Therefore, it would be beneficial to have a simple kink resistant device which may be attached to a flexible tubing to resist kinking of the tubing.

SUMMARY

The present disclosure is directed to a device for preventing kinking of a flexible tubing, the device can be easily moved and adjusted by a user. The device comprises a first clamp, a second clamp, a first rod and a second rod, wherein the first clamp and the second clamp carry the first rod and the second rod to form a frame, and the flexible tubing is secured to the first clamp and the second clamp.

In some embodiments, the clamp includes a main body, wherein the main body comprises a first arm having three half circles, a second arm having three other half circles. The three half circles and the three other half circles define three passages to receive the first rod, the second rod and the flexible tubing when the first arm and the second arm are in a closed position. the main body further comprises a hinge to connect the first arm and the second arm and the hinge is integrally formed with the first arm and the second arm. the clamp can further comprise two bolts on the outer sides of the passages.

In some embodiments, the clamp includes a first arm having two half circles and at least one side plate with at least one side plate having a through opening, a second arm having two other half circles and a middle plate having another through opening. The two half circles and the two other half circles define two passages to receive the first rod and the flexible tubing, the through opening of the at least one side plate and the through opening of the middle plate are aligned to form another passage to allow the second rod to pass through.

In some embodiments, the clamp includes a first arm having a half circle and at least two side plates on both sides of the half circle, each side plate has a through opening, a second arm having other half circle and at least two middle plates on both sides of the other half circle, wherein each middle plate has a through opening. The half circle and the other half circle define a passage to receive the flexible tubing, the through opening of the at least two side plates and the through opening of the at least two middle plates are aligned to form two other passages on both sides of the passage to allow the first rod and the second rod to pass through.

In some embodiments, the first rod and the second rod are made of steel, wood, or plastic. The first rod and the second rod can be straight. The first rod and the second rod can be bent. The first clamp and the second clamp can slide along the first rod and the second rod. In one embodiment, the first clamp and the second clamp can slide along the flexible tubing.

The device can be attached at any location along the tubing, allowing the tubing to bend past 90 degrees without kinking. Multiple devices can be used in series to route tubing in a desired route without it kinking.

An embodiment of the disclosure is a device for preventing kinking of a flexible tubing, comprising a first clamp; a first rod enclosed by the first clamp; a second clamp enclosing the first rod; a second rod enclosed by the first clamp and the second clamp, wherein the first rod is also enclosed by the second clamp; wherein the first clamp and the second clamp carry the first rod and the second rod to form a frame, wherein the frame provides a location for the flexible tubing to be detachably secured to the first clamp and the second clamp. In an embodiment, each of the first clamp and the second clamp comprises a main body comprising: a first arm comprising three half circles; a second arm comprising three other half circles; wherein the three half circles of the first arm and the three half circles of the second arm define three passages to receive the first rod, the second rod, and the flexible tubing when the first arm and the second arm are in a closed position. In an embodiment, the main body further comprises a hinge connecting the first arm and the second arm. In an embodiment, the hinge is integrally formed with the first arm and the second arm. In an embodiment, the device further comprises a bolt at the end of the clamp opposite to the hinge. In an embodiment, the device further comprises a bolt on each outer edge of the clamp. In an embodiment, the first clamp and the second clamp comprise: a first arm comprising two half circles and at least one side plate wherein each side plate comprises a through opening; a second arm comprising two other half circles and a middle plate having another through opening; wherein the two half circles of the first arm and the two half circles of the second arm define two passages to receive the first rod and the flexible tubing, and wherein the through opening of the at least one side plate and the through opening of the middle plate are aligned to form a third passage to allow the second rod to pass through. In an embodiment, the main body further comprises a hinge to connect the first arm and the second arm. In an embodiment, the hinge is integrally formed with the first arm and the second arm. In an embodiment, the first clamp and the second clamp comprise: a first arm having a half circle and at least two side plates on each side of the half circle, wherein each of the at least two side plates has a through opening; a second arm having a half circle and at least two middle plates on each side of the other half circle, wherein each middle plate has a through opening; wherein the half circle of the first arm and the half circle of the second arm define a passage to receive the flexible tubing, the through opening of the at least two side plates and the through opening of the at least two middle plates are aligned to form passages on both sides of the passage to allow the first rod and the second rod to pass through. In an embodiment, the first rod and the second rod are made of steel, wood, or plastic. In an embodiment, the first rod and the second rod are straight. In an embodiment, the first rod and the second rod can be bent. In an embodiment, the first clamp and the second clamp can slide along the first rod and the second rod. In an embodiment, the first clamp and the second clamp can slide along the flexible tubing. In an embodiment, the flexible tubing is tubing for providing oxygen therapy.

An embodiment of the disclosure is a system of preventing kinking of tubing comprising attaching the device to tubing.

An embodiment of the disclosure is a method of manufacturing a device for preventing kinking of a flexible tubing comprising forming a first clamp and a second clamp; obtaining a first rod and a second rod; placing the first rod through a first passage in the first clamp and placing the second rod through a second passage in the first clamp; and placing the first rod through a first passage in the second clamp and placing the second rod through a second passage in the second clamp. In an embodiment, the first and second clamp are formed by at least one process selected from the group consisting of 3-D printing, computer numerical control machining, polymer casting, rotational molding, vacuum forming, injection molding, extrusion, and blow molding.

An embodiment of the disclosure is a method of use comprising attaching the device to tubing. In an embodiment, the device is attached to tubing by sliding the tubing through the center passage or by unfastening the clamps and fastening them around the tubing.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which:

FIG. 5 is a prospective view of a clamp in accordance with another embodiment of the present disclosure;

FIG. 6 is a prospective view of the first arm of the clamp in FIG. 5;

FIG. 7 is a prospective view of the second arm of the clamp in FIG. 5;

FIG. 8 shows a schematic view of an anti-kinking device secured to a tubing;

FIG. 9 shows a schematic view of an anti-kinking device with bent rods secured to a tubing;

FIG. 10A-10D show an alternative embodiment in which the same design piece is used for the top and bottom of the clamp. FIG. 10A depicts a perspective view of the design piece. FIG. 10B depicts a side view of the design piece. FIG. 10C depicts a top view of the design piece. FIG. 10D depicts a side view of two design pieces assembled together;

FIG. 11A shows a top-view of the clamp, FIG. 11B shows a side-view of the clamp, and FIG. 11C shows a cut-through end view of the clamp;

FIG. 12A-12D show a snap-together clamp design. FIG. 12A shows a top-view of the clamp, FIG. 12B shows a side-view of the clamp, FIG. 12C shows a cut-through end view of the clamp, and FIG. 12D shows the lower right-quadrant of FIG. 12B;

FIG. 13A shows a top-view of the rods and FIG. 13B shows a side-view of the rods;

FIG. 14A shows a top-view of the rods and FIG. 14B shows a side-view of the rods;

FIG. 15A shows a top-view of the rods and FIG. 14B shows a side-view of the rods; FIG. 16A shows a top-view of the rods and FIG. 16B shows a side-view of the rods.

DETAILED DESCRIPTION

The particulars shown herein are by way of example and for purposes of illustrative discussion of the embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary $3^{rd}$ Edition.

Figure 1:
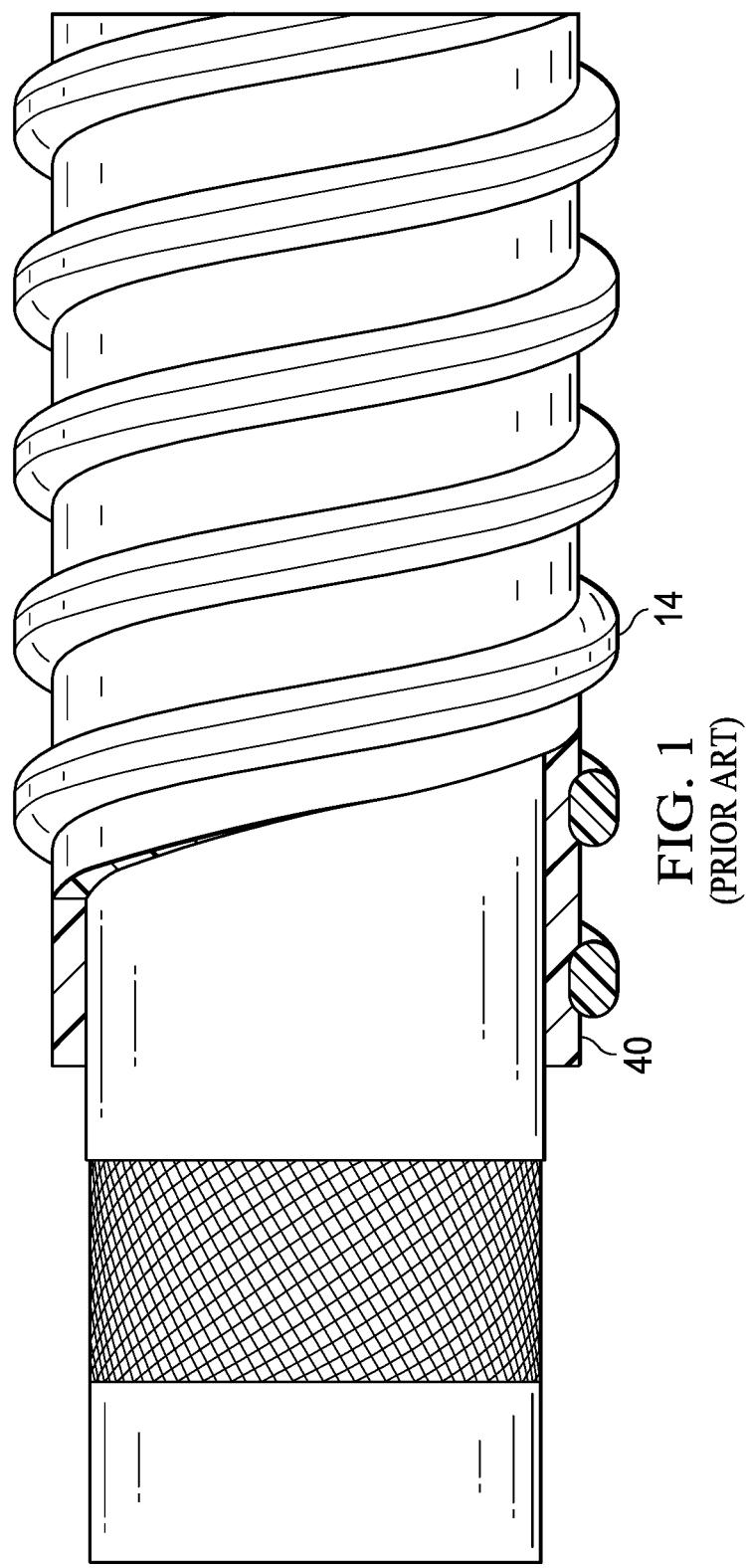
FIG. 1 shows a prior art hose with a spiral metal wire.
Figure 2:
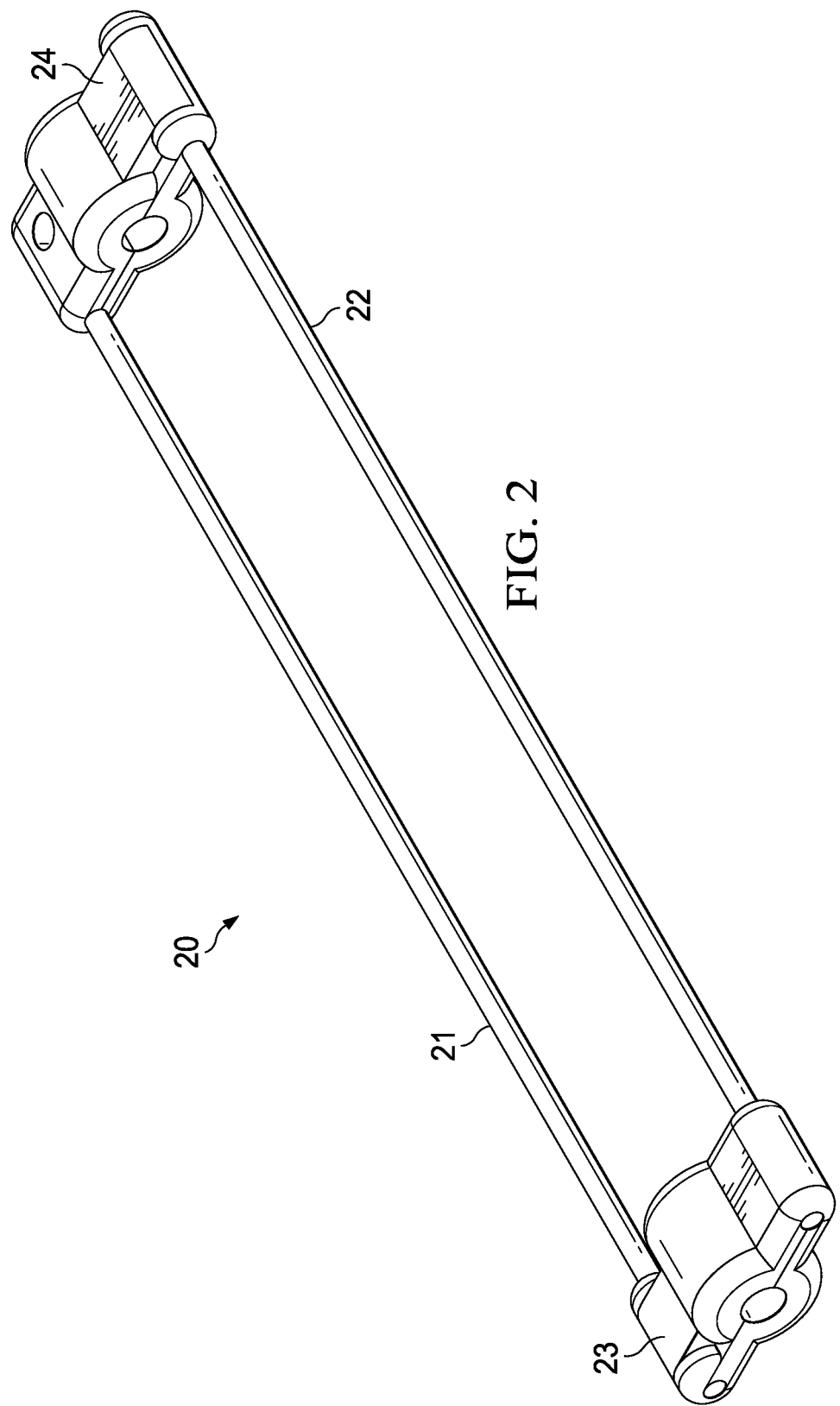
FIG. 2 shows a schematic view of an anti-kinking device in accordance with an embodiment of the present disclosure.

FIG. 2 illustrates an embodiment of an anti-kinking device 20 of the present disclosure. The device 20 has two connecting heads 23, 24 which carry two rods 21, 22 disposed parallel to one another. The two connecting heads 23, 24 and the two rods 21, 22 form a square plane frame. The anti-kinking device 20 can be attached to any location along a flexible tubing (not shown in FIG. 2) by detachably securing the tubing to the two connecting heads 23, 24. The two connecting heads 23, 24 can restrict axial movement and twist of the tubing therebetween, such that the portion of tubing between the connecting heads 23, 24 will not kink. The detachable securing can be any pattern known to one of skill in the art, including but not limit to binding, lashing, clamping and pasting. In an embodiment, the device can be used for any type of tubing or hoses, include medical tubing, industrial applications, and gardening applications. In an embodiment, the size of the device can be any size needed to fit the particular diameter of tubing or hose.

Figure 3:
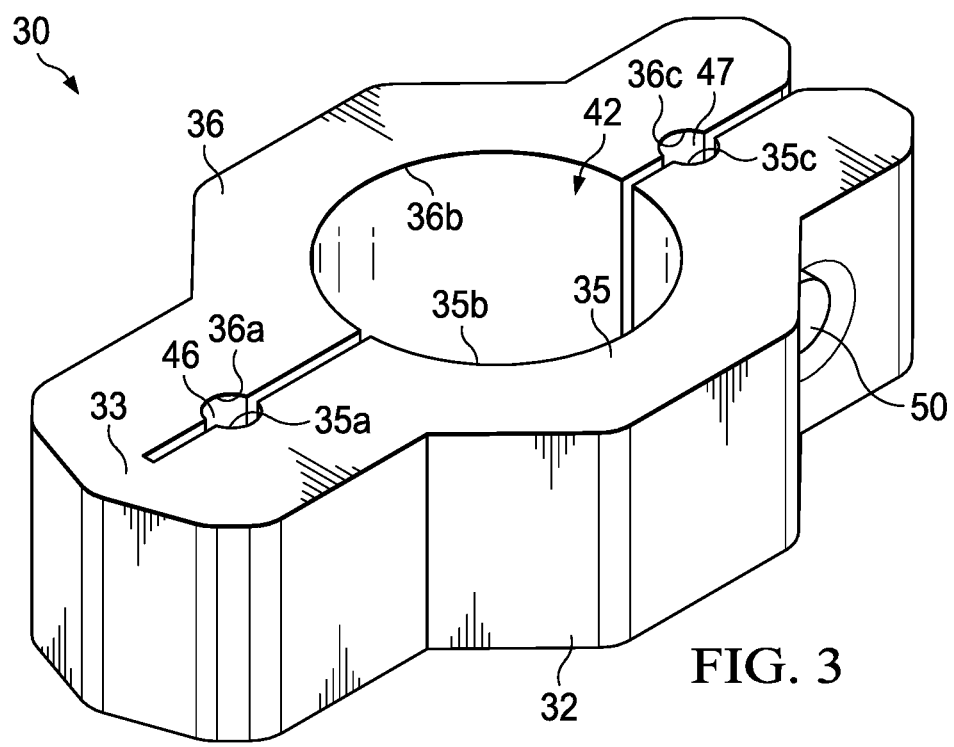
FIG. 3 is a prospective view of a clamp in accordance with an embodiment of the present disclosure.
Figure 4:
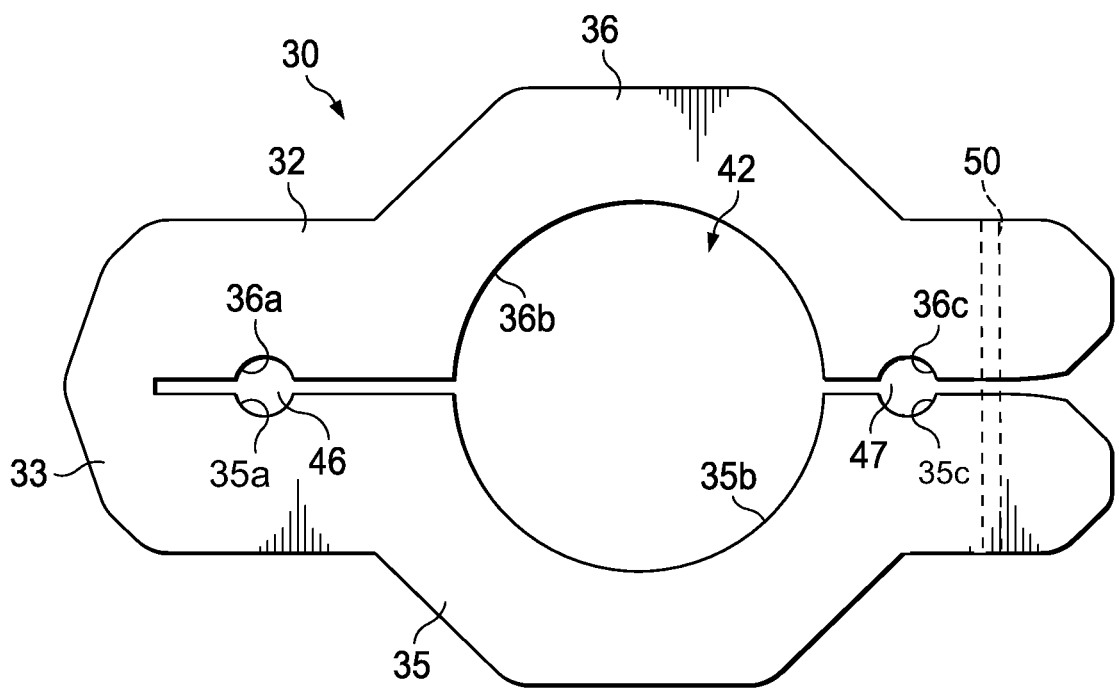
FIG. 4 is a sectional view of a clamp of FIG. 3.

In one embodiment, the connecting head can be a clamp. Referring to FIGS. 3 and 4, the clamp 30 has a main body 32 which may be formed of any appropriate hard material such as steel, wood, or the like. In an embodiment, the main body 32 is made of thermoplastic elastomer. As used herein, the word "elastomer' and any derivatives of that word are meant to include any thermo-setting material, either natural or synthetic, including natural and synthetic rubber, nitrile rubber, butyl rubber, polysulfide rubber, TPO rubber, and polyurethane rubber. In an embodiment, polyurethane elastomer can be used for the body, other such elastomers can also function to serve as the body of the clamp, according to the present disclosure. In an embodiment, the clamp can be made of polyvinyl chloride, polyethylene, polypropylene, polystyrene, thermoplastic elastomers, thermoplastic polyurethane, polycarbonate, nylon, or polyvinylidene difluoride. In an embodiment, the clamps are made of an antimicrobial material. In an embodiment, the clamps are made of an antibacterial material. In an embodiment, the clamps are made of an antifungal material. In an embodiment, the clamps are made of an antiviral material. In an embodiment, the clamps are made of stainless steel, acrylic, polyester, copper, silver, organosilanes, dimethyloctadecyl (3-trimethoxysilyl propyl) ammonium chloride, alkyldimethylbenzylammonium chloride, didecyldimethylammonium chloride, or nanomaterials including, but not limited to, titanium dioxide, zinc oxide, magnetite, magnesium oxide, gold, silver, copper, gallium, and carbon nanotubes.

In an embodiment, the clamps can be created by any plastic manufacturing process. In an embodiment, the clamps can be created using at least one of the following processes: 3-D printing, computer numerical control machining, polymer casting, rotational molding, vacuum forming, injection molding, extrusion, and blow molding. In one embodiment, the clamp 30 can be formed by 3-D printing technology.

In an embodiment, the main body 32 includes a pair of arms 35 and 36 connected by a hinge 33 which is an integral of the main body 32. The arm 35 has three half circles 35a, 35b and 35c, and arm 36 has corresponding three half circles 36a, 36b and 36c. The half circles are configured such that when the arms 35 and 36 are pivoted around the hinge 33 to a closed position as shown in FIG. 3, they define three passages 46, 42, and 47 to receive two rods 21, 22 and a flexible tubing (not shown in FIG. 3). The passage 46 near the hinge 33 is referred to as a proximal passage, the passage 47 furthest from the hinge 33 is referred to as distal passage, and the middle passage 42 is between the proximal passage 46 and distal passage 47. The proximal passage 46 and distal passage 47 each receive a rod 21, 22 and the middle passage 42 receives a flexible tubing.

The main body 32 also includes a through hole 50 which is used to receive a fastening device (not shown in FIG. 3) such that the fastening device can pull the two arms closer together to clamp around the rods and flexible tubing. In an embodiment, the fastening device is a bolt. In one embodiment, the through hole 50 is located at the opposite end of the hinge.

In another embodiment, referring to FIGS. 5, 6 and 7, the clamp 30 includes two separable arms 35, 36, connected by a hinge 33. The hinge 33 has a first hinge element 33a on arm 35 and a second hinge element 33b on arm 36. Although the hinge in this embodiment is a separate component from the main body of the clamp, the hinge 33 can also be an integral of the main body. Arm 35 has two half circles 35a and 35b and arm 36 has corresponding two half circles 36a and 36b. The half circles are configured such that when the arms 35 and 36 are pivoted around the hinge 33 to a closed position as shown in FIG. 5, they define passages 46, 42, and 47 to receive a first rod of the anti-kinking device 20 and a flexible tubing (not shown in FIG. 5) and a second rod.

Referring to FIG. 6, the arm 35 has two side plates 60 and 62 which are located at the opposite end of the hinge 33a. The two side plates 60 and 62 are joined to the arm 35 by two intermediate portions 61, 63 respectively to provide a unitary structure of arm 35. Referring to FIG. 7, the arm 36 has a middle plate 64 which is located at the opposite end of the hinge 33. The middle plate 64 is joined to the arm 36 by an intermediate portion 68 to provide a unitary structure of arm 36.

There is a distance between the two side plates 60 and 62 (FIG. 6). The through openings 65 and 67 of the two side plates 60 and 62 are aligned. The middle plate 64 also has a through opening 70 (FIG. 7). The distance between the two side plates 60 and 62 is configured such that when the arms 35 and 36 are pivoted around the hinge 33 to a closed position as shown in FIG. 5, the two side plates 60 and 62 accommodate the middle plate 64 of the arm 36. At the closed position, the three through openings 65, 67, and 70 are aligned to form a passage 47 to allow a second rod 22 of the anti-kinking device 20 to pass through. The second rod 22 of the anti-kinking device 20 can pull the two arms 35 and 36 closer together to clamp around the first rod and the flexible tubing. Therefore, there is no need for a bolt in this embodiment to grip the clamp.

In some embodiments, the arm 35 has only one side plate and arm 36 has another side plate, and each of the two side plates has a through opening. In the closed position, the two side plates can be assembled such that the two through opening are aligned to form a passage 47 to allow a second rod of the anti-kinking device 20 to pass through and the second rod of the anti-kinking device 20 can pull the two arms 35 and 36 closer together to clamp around the first rod and the flexible tubing.

In some embodiments, the clamp 30 does not have a hinge or bolt. In an embodiment, the main body of the clamp includes a pair of identical separate arms. Each of the arms has three half circles. The half circles are configured such that when the two arms are held together to a closed position as shown in FIG. 3, they define three passages 46, 42, and 47 to receive two rods of the anti-kinking device 20 and a flexible tubing (not shown in FIG. 3). The main body of the clamp further includes two through holes which are used to receive two fastening devices respectively such that the fastening devices can pull the two arms closer together to clamp around the rods and flexible tubing. In an embodiment, the fastening devices are bolts. In one embodiment, the two through holes are located on two opposite ends of the main body.

In some embodiments, the clamp 30 does not need a hinge or bolt. In an embodiment, a spring clip can be used.

In an embodiment, the main body of the clamp includes a pair of separate arms. Each of the arms has one half circle. The half circles are configured such that when the two arms are held together to a closed position, they define a passage 42 to receive a flexible tubing (tubing not shown in FIG. 5). Each of the arms can include side plates on both sides of the half circle, joining to the arm by intermediate portions respectively to provide a unitary structure. Each of the side plates has a through opening. The side plates can be assembled such that, when the two arms are held together, the through openings are aligned to form two passages 46 and 47 (as shown in FIG. 5). Passages 46 and 47 are on each side of the passage 42 and to allow a rod of the anti-kinking device 20 to pass through each passage 46 and 47. The two rods of the anti-kinking device 20 can pull the two arms closer together to clamp around the flexible tubing.

Referring to FIG. 8, an anti-kinking device can include a first clamp 23, a second clamp 24, a first rod 21, and a second rod 22. The two clamps grip the two straight rods 21, 22 and a flexible tubing 80. In an embodiment, the tubing 80 is parallel to the two rods. The frame formed by the two clamps and the two rods can restrict axial movement and twist of the tubing 80 such that the portion of tubing between the clamps 23, 24 will not kink. The clamps can be any kinds of clamps mentioned above and the rods can be made of any appropriate hard material such as steel, wood, plastic, or the like.

In some embodiments, the flexible tubing 80 is a medical tubing to carry oxygen to a patient. The medical tubing can be made out of several types of plastic, including polyvinyl chloride (PVC), polyethylene, thermoplastic elastomers (TPE), nylon, and silicone.

In some embodiments, after the tubing 80 is secured to the anti-kinking device, the two clamps 23, 24 can slide on the two rods 21, 22 and the tubing 80 to adjust the distance between the two clamps 23, 24, which can adjust the distance of portion of the tubing need to anti-kink. In an embodiment, the two clamps 23, 24 can slide on the tubing 80 synchronously to keep distance between them, while securing the anti-kinking device to different portions of tubing. Some prior art anti-kinking device just protect hose or cables at the ends whereas the present device can be at any position along the length of the tubing.

In some embodiments, the rods are made of steel and can be bent to route a tubing in a desired route without kinking. Referring to FIG. 9, an anti-kinking device include a first clamp 23, a second clamp 24, a first rod 21, and a second rod 22. The two clamps grip the two rods and a flexible tubing 80 by two bolts 54. The first rod 21 is bent through a specified angle at two points near the two clamps and the second rod 22 is bent correspondingly. The tubing 80 will bent a corresponding angle which will change the route of the tubing 80. The position and angle of the bend can be determined by the desired route of the tubing. For example, the range of the angle is between 80 degree to 180 degree. In some embodiments, the bend angle is 90 degrees. In some embodiments, multiple anti-kinking devices can be used in series to route a tubing in desired route without kinking.

Figure 10C:
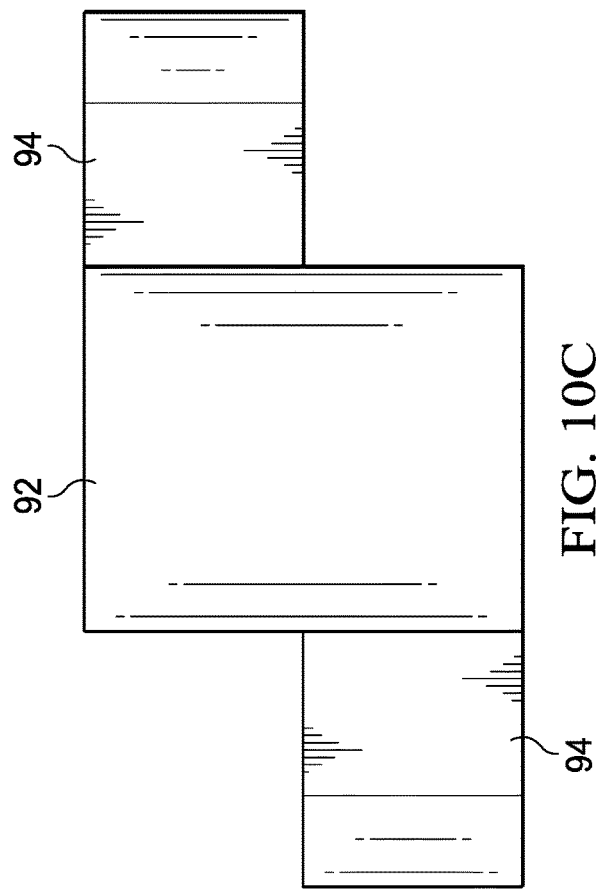
Figure 10D:
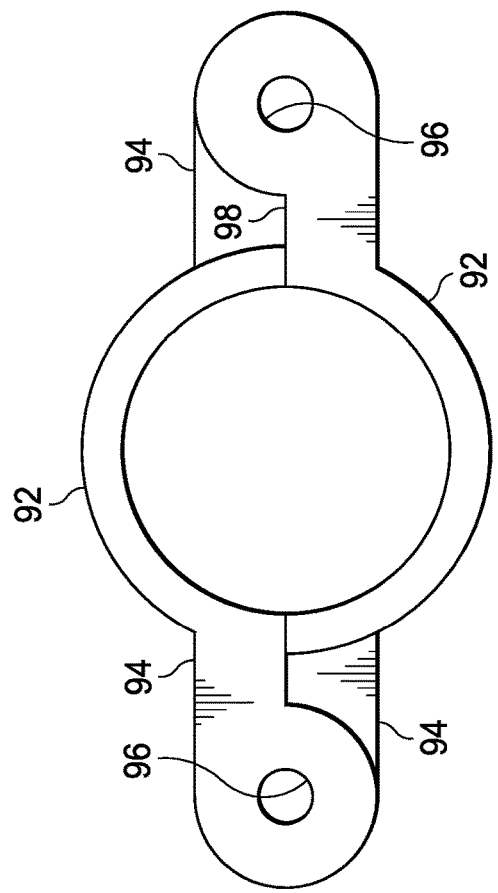

FIG. 10A-10D shows an alternative embodiment for a clamp. This embodiment uses the same design piece 90 for the top and bottom of the clamp. FIG. 10A depicts a perspective view of the design piece. Side passage 96 is present in intermediate portion 94. Half-circle piece 92 forms half of a central passage. FIG. 10B depicts a side view of the design piece. FIG. 10C depicts a top view of the design piece. FIG. 10D depicts a side view of two design pieces assembled together. Two intermediate portions 94 assemble together to form an arm 98.

Figure 11A:
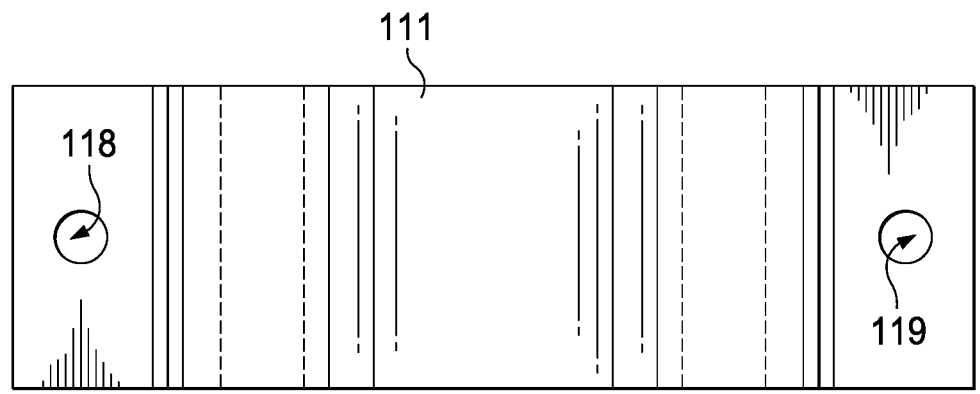
FIG. 11A-11C show a bolted clamp design.
Figure 11B:
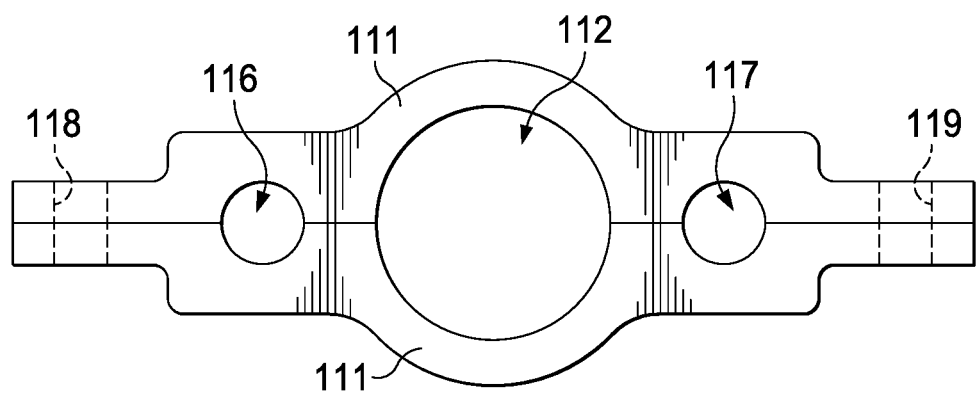
Figure 11C:
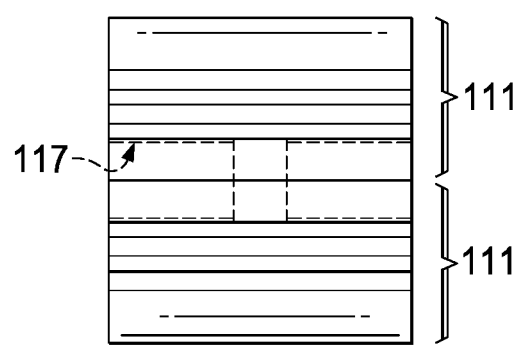

In some embodiments, the clamp is bolted together. FIG. 11A-11C show a bolted clamp design. FIG. 11A shows a top-view of the clamp. Identical pieces 111, 111 form the two portions of the clamp. FIG. 11A shows the top-view of 111. Openings 118 and 119 are capable of receiving a fastener, including but not limited to, a bolt. FIG. 11B shows a side-view of the clamp. Pieces 111 and 111 are shown in a configuration in which the bottom of one piece 111 is adjacent to the bottom of another piece 111 to form the clamp. Passages 116 and 117 are capable of receiving rods. Passage 112 is capable of receiving a hose. FIG. 11C shows a cut-through end view of the clamp. Pieces 111 and 111 are shown along with passage 117. The bolted clamp design is similar to the clamp made with a hinge and held together by the bolt, but in this embodiment, the clamp does not have the hinge function. This embodiment is made up of the two pieces of the clamp laying flush together and being bolted into place.

In some embodiments, the clamp snaps together. FIG. 12A-12D show a snap-together clamp design. FIG. 12A shows a top-view of the clamp. Piece 121 is shown. FIG. 12B shows a side-view of the clamp. The clamp comprises piece 121 and piece 128. Piece 121 and piece 128 snap together by a friction fit of peg 122 and hole 123. Passages 124, 126, and 127 are formed by piece 121 and 128. FIG. 12C shows a cut-through end view of the clamp. Pieces 121 and 128 are shown along with peg 122 and hole 123. FIG. 12D shows the lower right-quadrant of FIG. 12B. A portion of piece 128 is shown with peg 122 and part of passage 127. The snap together design is similar to the bolted clamp in that the pieces of the clamp lay flush together, but they are held together with a peg-in-hole type design. This friction-based connection can be used to interlock multiple components. This makes the clamp easy to snap together and take apart without strain, but also will stay together when in use.

Figure 13A:
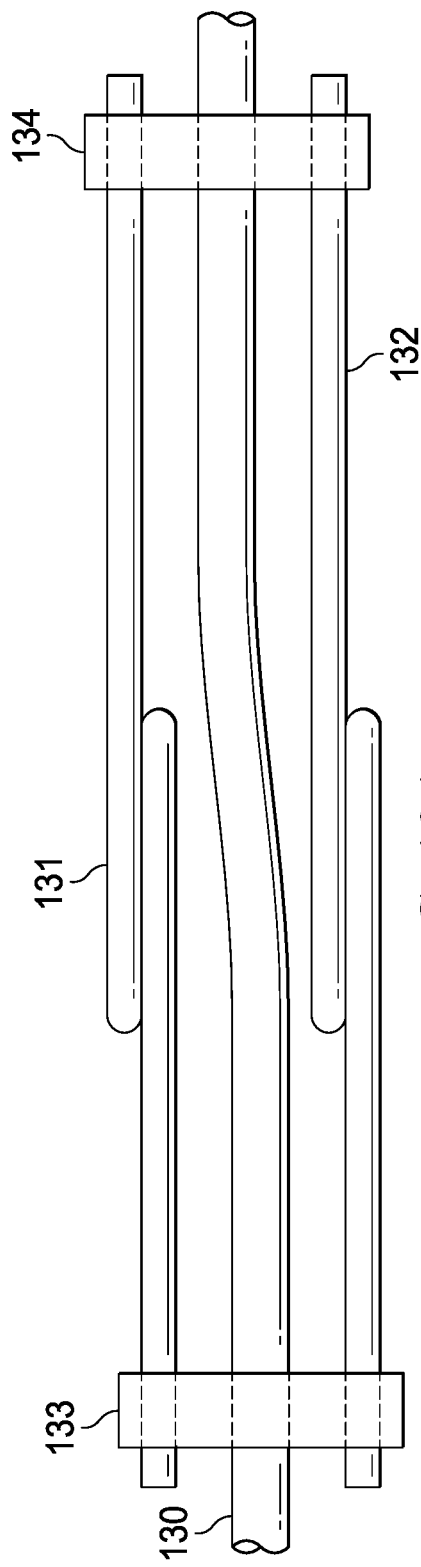
FIG. 13A-13B show spring connecting rods.
Figure 13B:
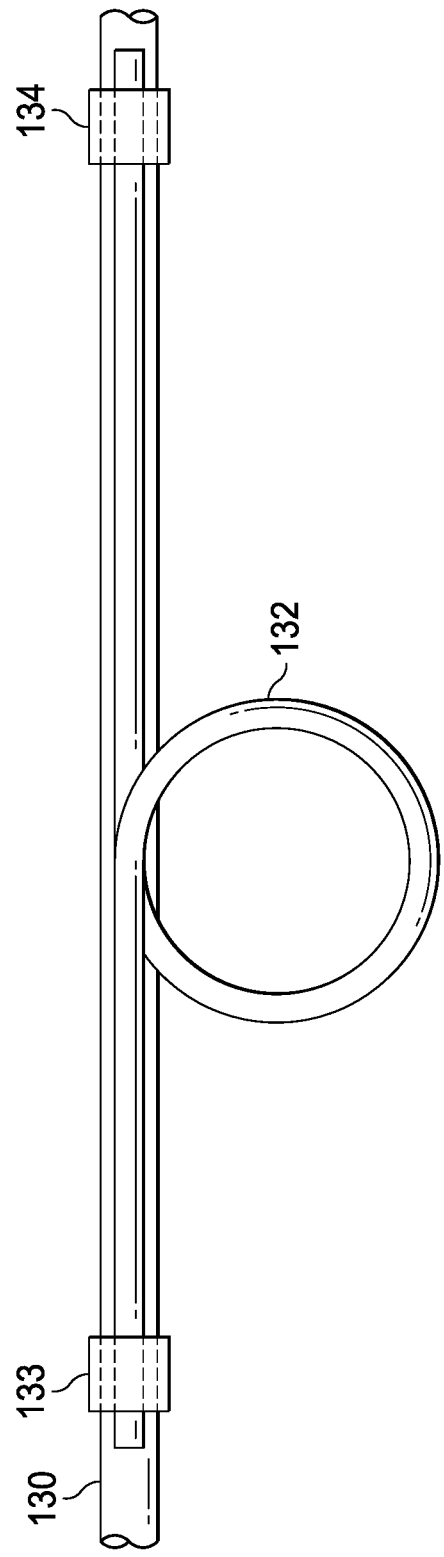

In some embodiments, the connecting rods are springs. FIG. 13A-13B show spring connecting rods. FIG. 13A shows a top-view of the rods. Rods 131 and 132 along with hose 130 pass through clamps 133 and 134. In this embodiment, rods 131 and 132 form at least part of a helix. FIG. 13B shows a side-view of the rods. Rod 132 is shown along with hose 130 and clamps 133 and 134. This spring-like design will allow flexibility around the hose or tubing so that the housing of the tubing can easily move when needed and return to original form without placing strain on the tubing or constricting flow through the tubing.

Figure 14A:
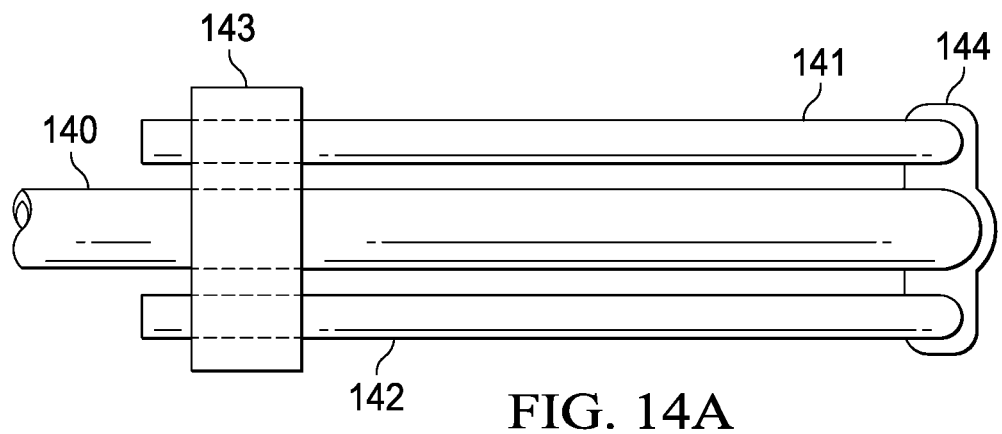
FIG. 14A-14B show pre-bent, rigid connecting rods.
Figure 14B:
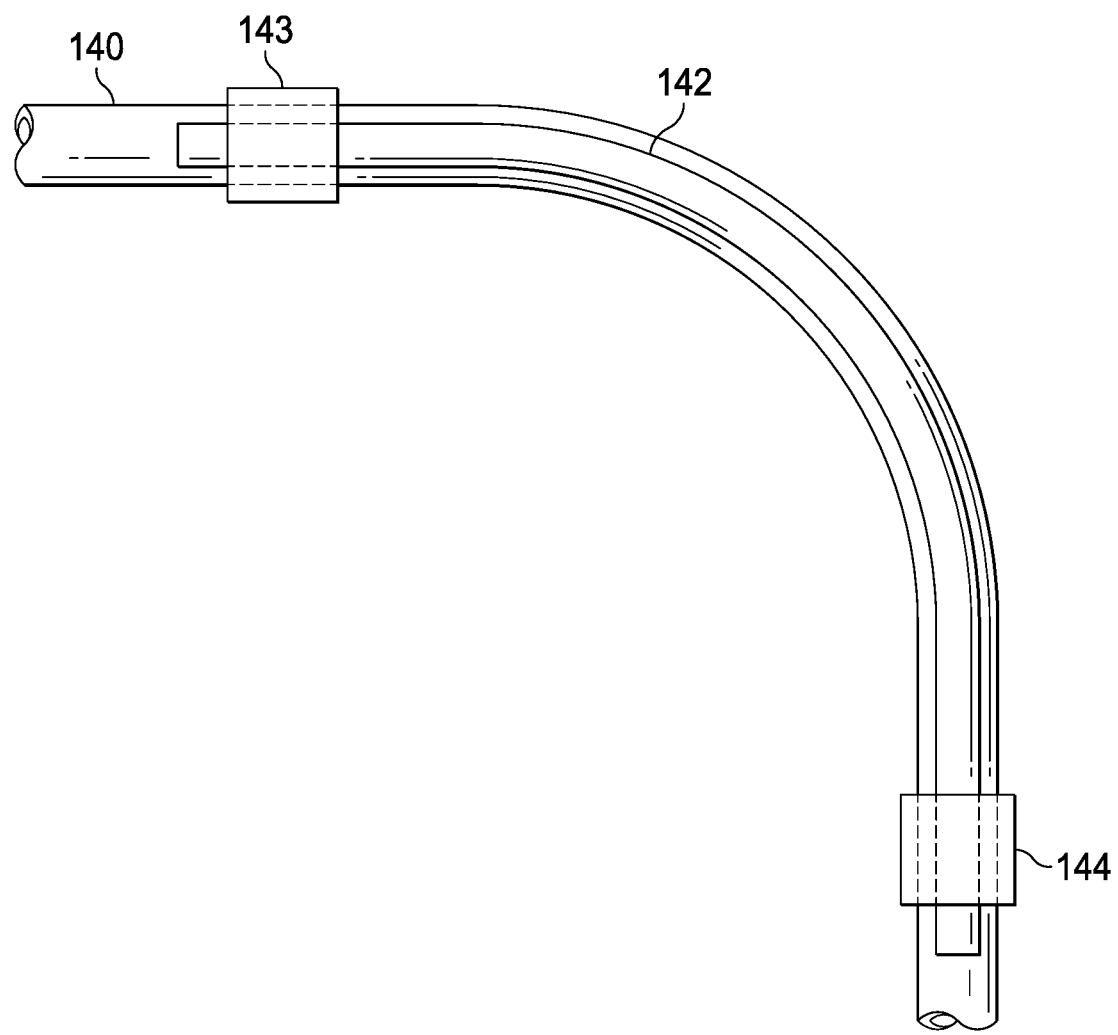

In some embodiments, the connecting rods are pre-bent and rigid. FIG. 14A-14B show pre-bent, rigid connecting rods. FIG. 14A shows a top-view of the rods. Rods 141 and 142 along with hose 140 pass through clamps 143 and 144. FIG. 14B shows a side-view of the rods. Rod 142 is shown along with hose 140 and clamps 143 and 144. By having pre-bent rods that hold their form at all times, the hose or tubing is able to bend at angles including, but not limited to, 90° to go around a corner and so on. By having a ridged rod system this allows the tubing to bend and be held in place this function works well for oxygen tubes specifically. When using portable oxygen units, the way the tubing hangs out of the backpack or carrying device the tubing starts to bend and can restrict airflow.

Figure 15A:
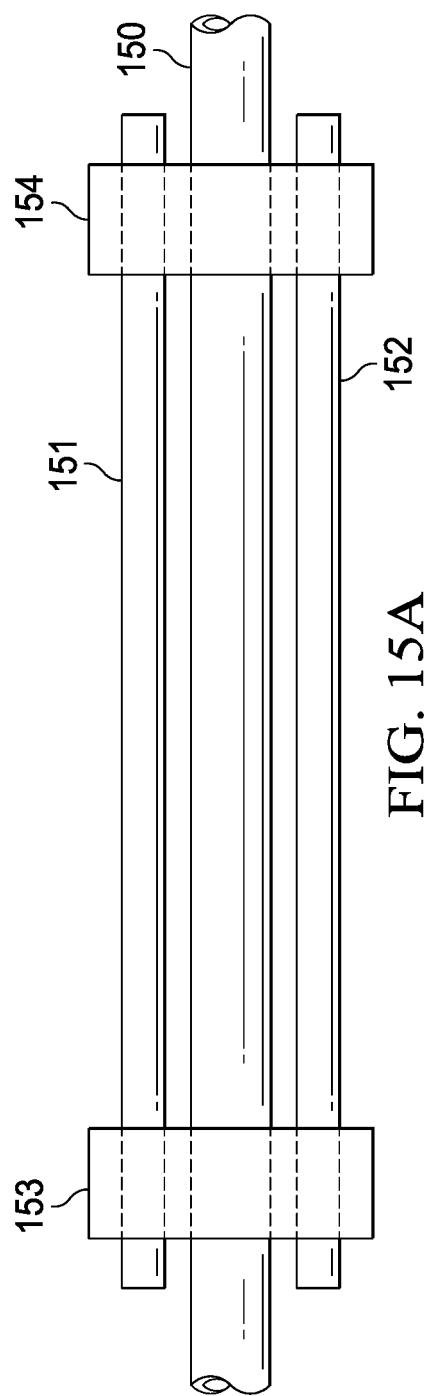
FIG. 15A-15B show straight, rigid connecting rods.
Figure 15B:
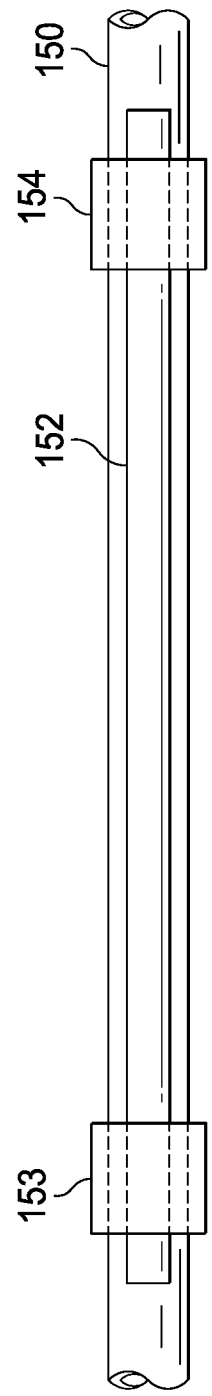

In some embodiments, the connecting rods are straight and rigid. FIG. 15A-15B show straight, rigid connecting rods. FIG. 15A shows a top-view of the rods. Rods 151 and 152 along with hose 150 pass through clamps 153 and 154. FIG. 15B shows a side-view of the rods. Rod 152 is shown along with hose 150 and clamps 153 and 154. With the straight and rigid connecting rod system this hold the hose or tubing in place and prevents the tubing from bending where it needs to be straight, this can be beneficial for tubing that has been coiled up and tends to have a bend in it but needs to be held a straight or leveled place.

Figure 16A:
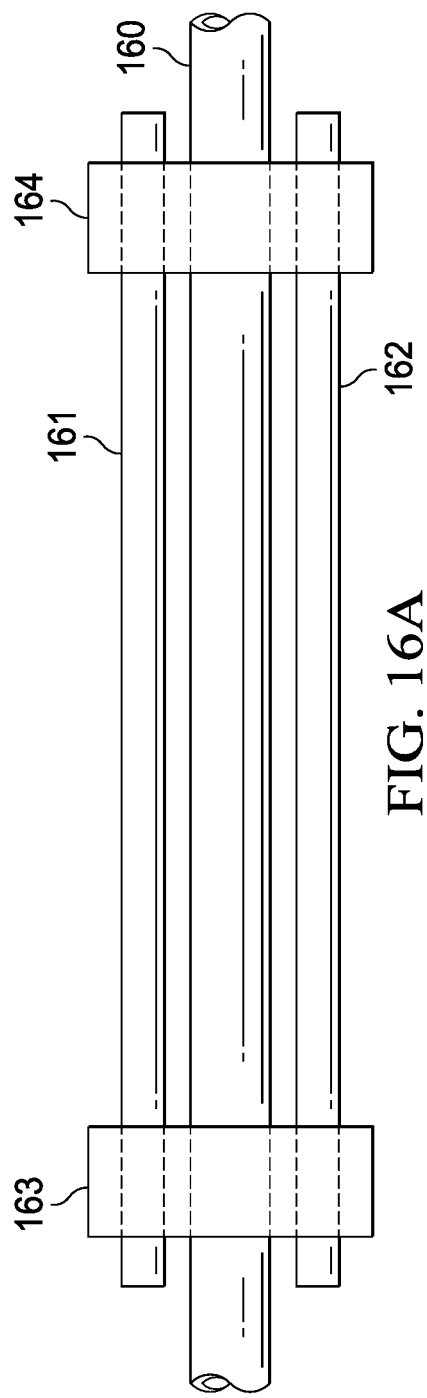
FIG. 16A-16B show user bendable, connecting rods.
Figure 16B:
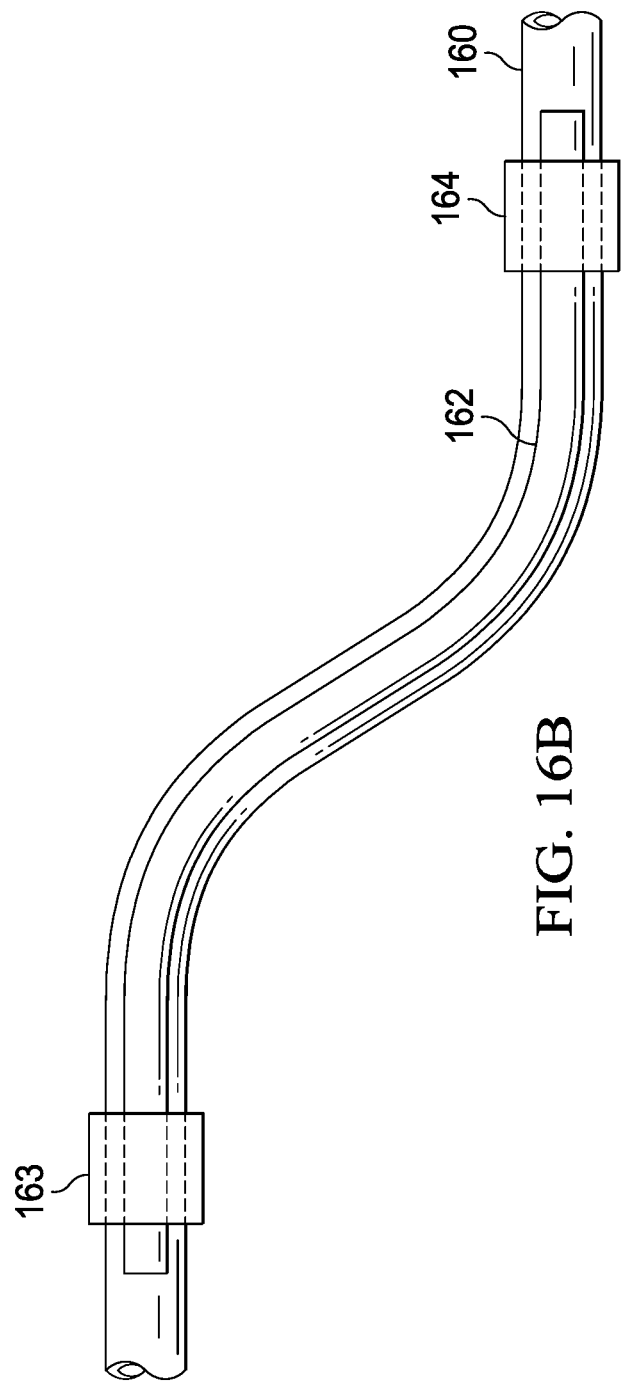

In some embodiments, the connecting rods are bendable by the user. FIG. 16A-16B show user bendable, connecting rods. FIG. 16A shows a top-view of the rods. Rods 161 and 162 along with hose 160 pass through clamps 163 and 164. FIG. 16B shows a side-view of the rods. Rod 162 is shown along with hose 160 and clamps 163 and 164. Some hoses or tubing may be used for different functions or need to be adjusted over time so by using bendable connecting rods the user can easily mold the rods to specific angles to meet their needs. By using a more malleable metal for the rods themselves the user can adjust the bend and shape as needed.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A device for preventing kinking of a flexible tubing, comprising
   a first clamp;
   a first rod enclosed by the first clamp;
   a second clamp enclosing the first rod;
   a second rod enclosed by the first clamp and the second clamp;
   wherein the first clamp and the second clamp carry the first rod and the second rod to form a frame; and
   wherein the first clamp and the second clamp each comprises:
   a first arm comprising two half circles and at least one side plate wherein each side plate comprises a through opening; and
   a second arm comprising two other half circles and a middle plate having another through opening;
   wherein one half circle of the first arm and one half circle of the second arm together define a first passage to receive the first rod, the other half circle of the first arm and the other half circle of the second arm together define a second passage to receive the flexible tubing, and wherein the through opening of the at least one side plate and the through opening of the middle plate are aligned to form a third passage to receive the second rod.

2. The device of claim 1, wherein each of the first clamp and the second clamp further comprises a hinge to connect the first arm and the second arm.

3. The device of claim 2, wherein a first hinge element is integrally formed with the first arm and a second hinge element is integrally formed with the second arm.

4. The device of claim 1, wherein the first rod and the second rod are made of steel, wood, or plastic.

5. The device of claim 1, wherein the first rod and the second rod are straight.

6. The device of claim 1, wherein the first rod and the second rod are bendable.

7. The device of claim 1, wherein the first clamp and the second clamp are slidable along the first rod and the second rod when the first clamp and the second clamp are closed and the first rod and the second rod have been received by the first and third passages.

8. The device of claim 1, wherein the first clamp and the second clamp are slidable along the flexible tubing when the first clamp and the second clamp are closed and the flexible tubing has been received by the second passages.

9. A system of preventing kinking of tubing, comprising:
   the device of claim 1 and
   tubing received by the first clamp and the second clamp of the device.

10. A method comprising:
    attaching the device of claim 1 to tubing.

11. The method of claim 10, wherein the tubing is flexible tubing for providing oxygen therapy.

12. A method of manufacturing a device for preventing kinking of a flexible tubing comprising
    forming a first clamp and a second clamp, wherein the first clamp and the second clamp each comprises:

a first arm comprising two half circles and at least one side plate wherein each side plate comprises a through opening; and a second arm comprising two other half circles and a middle plate having another through opening;

wherein one half circle of the first arm and one half circle of the second arm together define a first passage, and wherein the through opening of the at least one side plate and the through opening of the middle plate are aligned to form a second passage;

obtaining a first rod and a second rod;

placing the first rod through the first passage in the first clamp and placing the second rod through the second passage in the first clamp; and placing the first rod through the first passage in the second clamp and placing the second rod through the second passage in the second clamp.

13. The method of claim 12 wherein the first and second clamp are formed by at least one process selected from the group consisting of 3-D printing, computer numerical control machining, polymer casting, rotational molding, vacuum forming, injection molding, extrusion, and blow molding.

\* \* \* \* \*